United States Patent [19]

Balistreri et al.

[11] 4,241,017
[45] Dec. 23, 1980

[54] DEVICE FOR MEASURING A URINE DISCHARGE

[75] Inventors: Thomas W. Balistreri, Lake Bluff; Carl J. Steigerwald, Wauconda; Terry N. Layton, Arlington Heights; Frank K. Villari, Oak Park, all of Ill.; W. Martin Schultze, New Berlin, Wis.

[73] Assignee: The Kendall Company, Boston, Mass.

[21] Appl. No.: 32,820

[22] Filed: Apr. 24, 1979

[51] Int. Cl.³ .................. G01F 1/20; G01N 31/22
[52] U.S. Cl. .................... 422/58; 4/144.1; 73/215; 128/295; 128/760; 128/767; 128/771; 422/100; 422/102
[58] Field of Search .............. 422/58, 68, 100, 102; 128/760, 761, 767, 771, 295; 73/215; 4/144.1

[56] References Cited
U.S. PATENT DOCUMENTS

| | | |
|---|---|---|
| 3,831,446 | 8/1974 | Dye .................................. 73/194 R |
| 3,859,854 | 1/1975 | Dye et al. ............................. 73/215 |
| 3,871,230 | 3/1975 | Dye et al. ............................. 73/215 |
| 3,871,231 | 3/1975 | Ciarico ................................. 73/215 |
| 3,878,571 | 4/1975 | Seeley ............................. 128/767 X |
| 3,881,465 | 5/1975 | Raitto ................................ 128/760 |
| 3,884,072 | 5/1975 | Cheng ................................. 73/215 |
| 3,929,412 | 12/1975 | Villari ................................. 422/58 |
| 4,085,616 | 4/1978 | Patel et al. ........................... 73/215 |
| 4,100,802 | 7/1978 | Layton ................................. 73/215 |
| 4,131,016 | 12/1978 | Layton ................................. 73/215 |

Primary Examiner—Barry S. Richman
Attorney, Agent, or Firm—Powell L. Sprunger

[57] ABSTRACT

A device for measuring a discharge of urine comprising, a receiving member having an inlet port to receive the discharge, and a receptacle having a chamber to receive the discharge from the receiving member, and means for measuring a dynamic characteristic of the discharge. The device has a container attached to the receptacle to receive the discharge passing from the receptacle.

26 Claims, 24 Drawing Figures

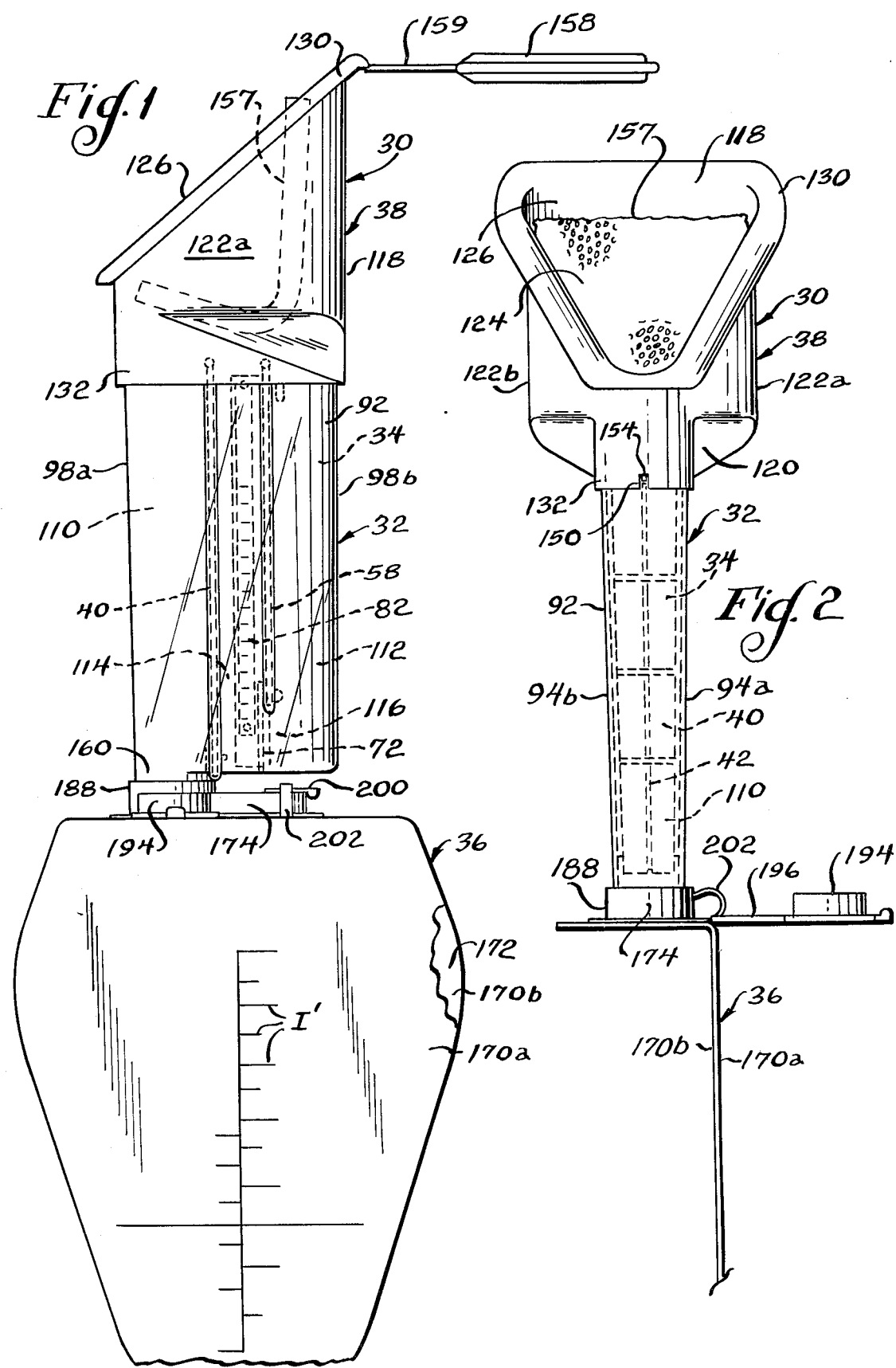

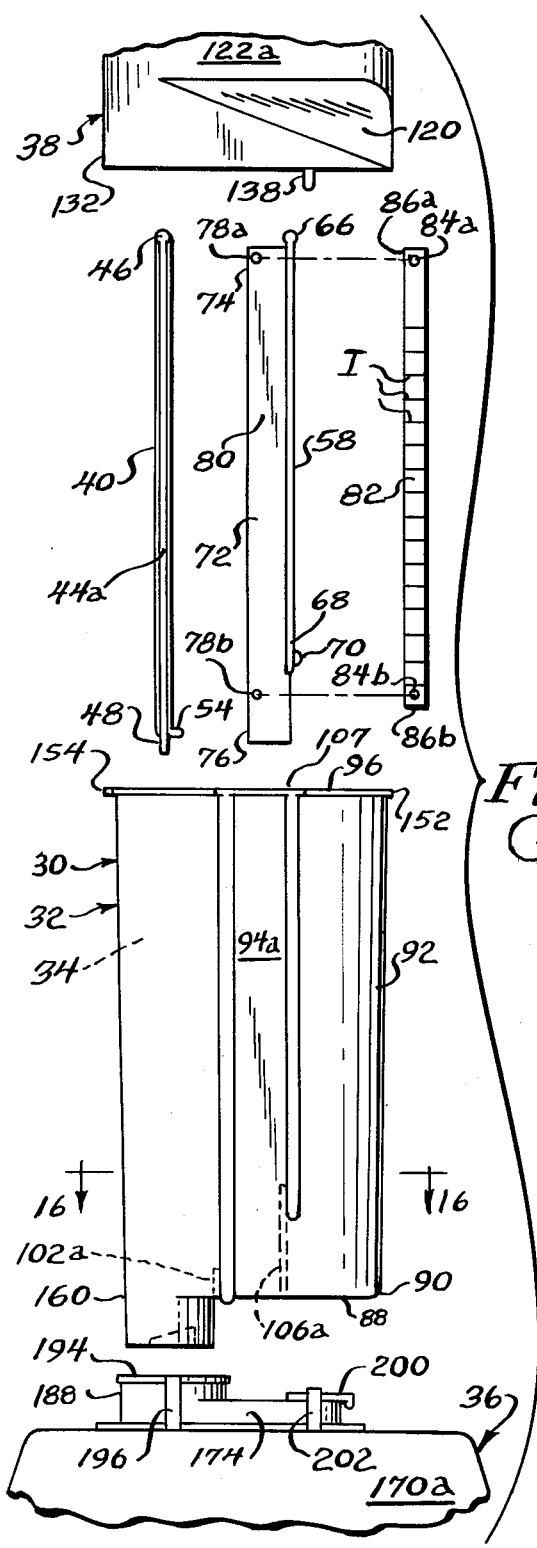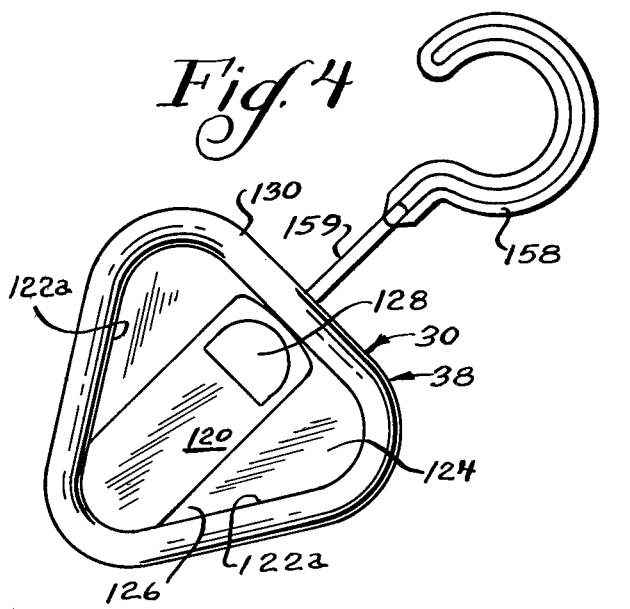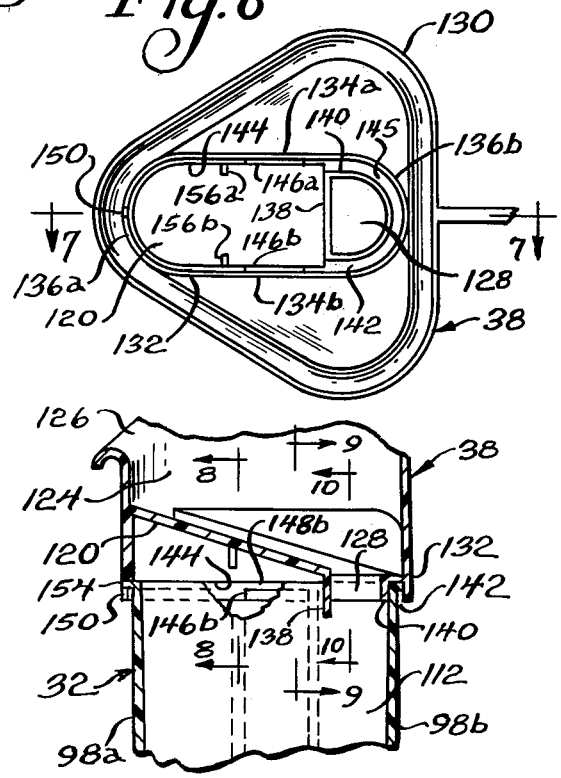

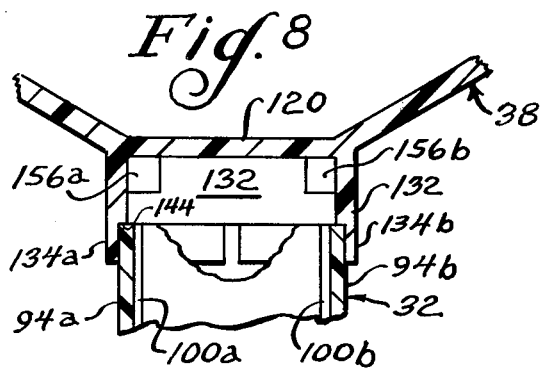
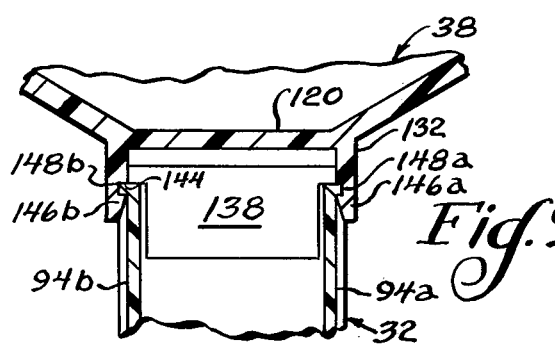
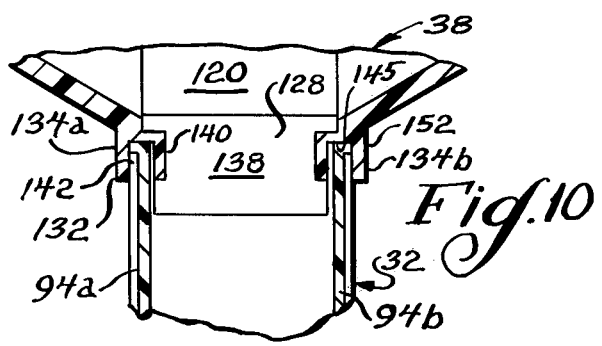
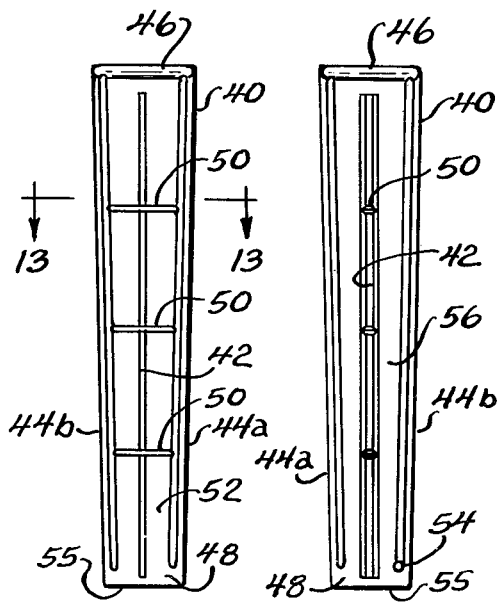
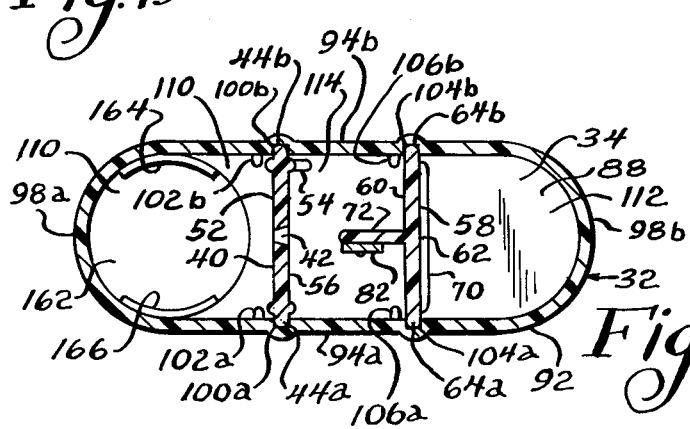
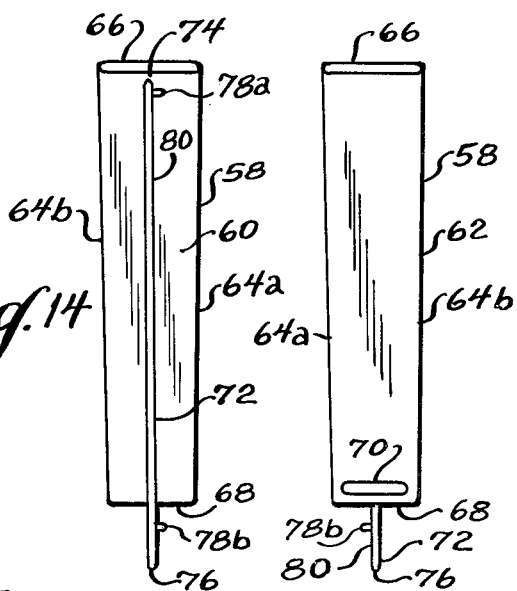

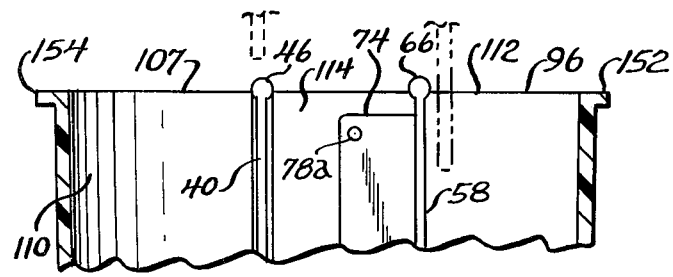
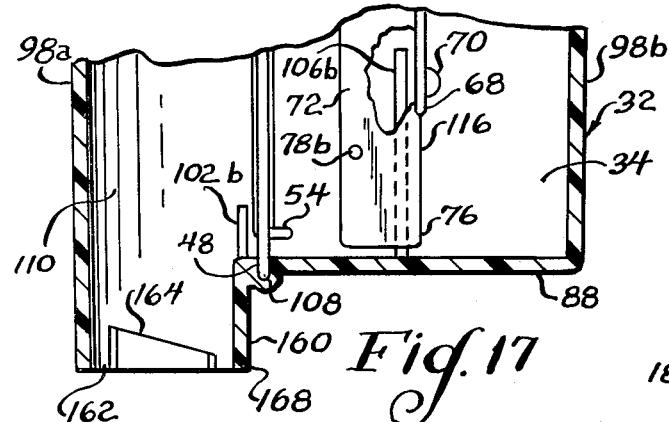
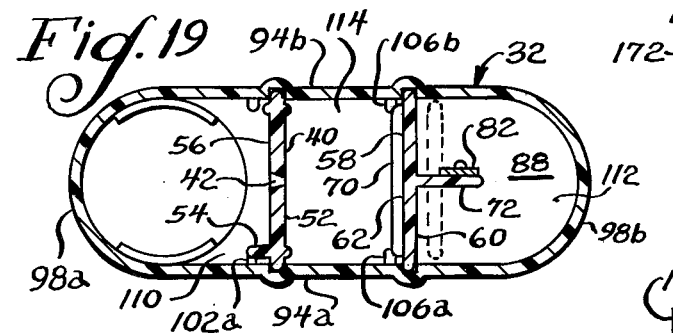
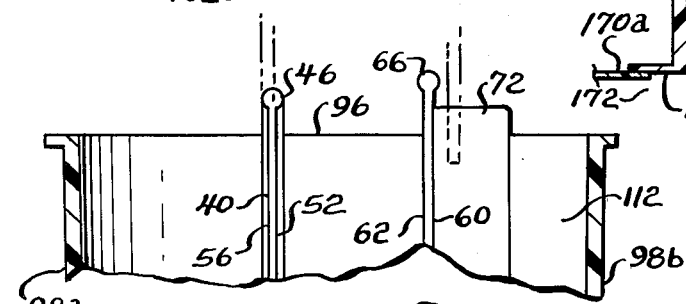
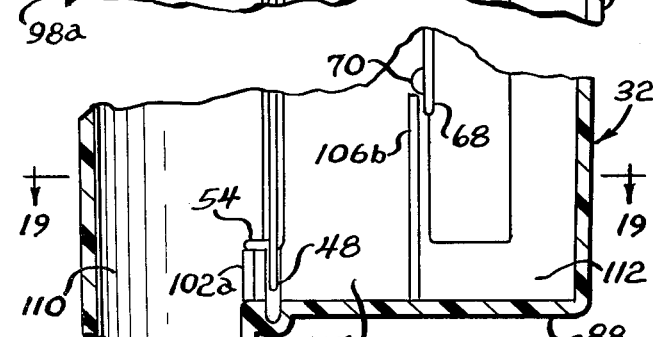
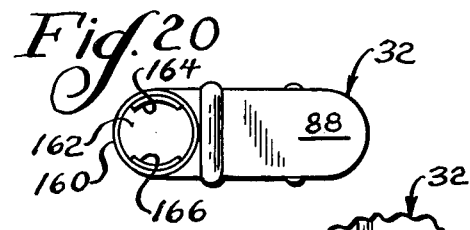
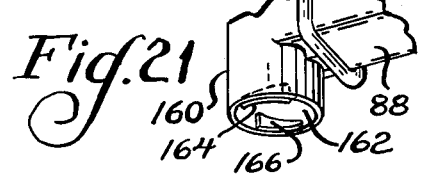
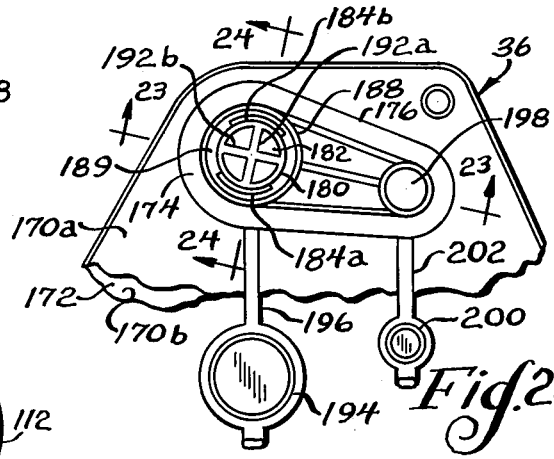
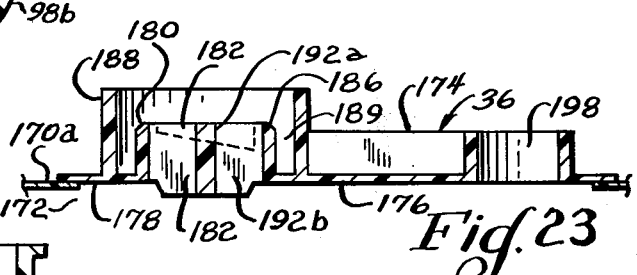
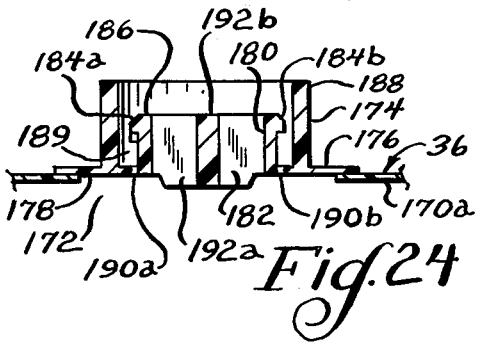

DEVICE FOR MEASURING A URINE DISCHARGE

BACKGROUND OF THE INVENTION

The present invention relates to liquid receiving devices, and more particularly to devices for measuring and collecting a discharge of urine.

In the past, it has been found desirable to obtain various data pertaining to a urine discharge. In particular, it was discovered that many urological problems could be readily diagnosed by analysing information obtained during the natural voiding of urine by patients. Presently, various types of devices are utilized to obtain data on the urine stream, such as total volume, average flow rate, force, velocity and configuration of the stream.

Many of these devices have suffered from less than total reliability because they have required the presence of one or more observers while the patient is voiding. It is obvious that administration of such devices in this manner creates sufficient psychological difficulties for many of the patients to effect voiding. Consequently, if the patients void at all, the potentially erroneous data obtained may result in a false diagnosis and a loss of confidence in the device by the physician. A further complication arises from the fact that many of these devices are rather bulky, and are somewhat difficult to use.

SUMMARY OF THE INVENTION

A principal feature of the present invention is the provision of a device of simplified construction for measuring and collecting a urine discharge, and which may be self-administered by a patient.

The device of the present invention comprises, a hollow receptacle having upright outer walls and a lower wall defining a chamber, and an elongated first upright plate extending laterally across the inside of the receptacle substantially the height of the chamber from the lower wall to a location adjacent an upper end of the receptacle, with the first plate defining a channel intermediate the first plate and an outer end wall of the receptacle, and with the first plate having slot means extending longitudinally along the first plate. The receptacle has an elongated upright second plate extending laterally across the inside of the receptacle from a location adjacent an upper end of the receptacle to a location adjacent a lower end of the receptacle, with the second plate defining a compartment intermediate the first and second plates, a passageway intermediate the second plate and an outer end wall of the receptacle, and a space adjacent the lower wall communicating between the passageway and the compartment. The container also has a lower tubular extension defining an outlet port for the receptacle chamber. The second plate has an outwardly extending indicating plate with a pair of spaced pins, and an indicating strip for measuring the height of liquid collected in the compartment. The device has a fluid receiving member attached to an upper end of the receptacle and having a lower wall and sidewalls defining a cavity, an inlet port communicating with the cavity for passage of the discharge into the cavity, and a lower outlet opening communicating with the cavity for passage of the discharge out of the cavity. The device also has a container with a support member for attachment to the tubular section with the channel communicating with a chamber in the container for passage of the discharge from the receptacle into the container.

A feature of the present invention is that the receiving member may be removed from the receptacle to provide access to the first and second plates.

Another feature of the invention is that the first and second plates may be removed from the receptacle for purposes of cleaning and sterilizing the plates and receptacle after use.

Yet another feature of the invention is that the indicating strip is retained on the indicating plate by the pair of spaced pins during use of the device.

Still another feature of the invention is that the second plate may be removed from the receptacle after usage of the device, another indicating strip may be placed upon the indicating plate after removal of the used indicating strip, and the second plate may again be placed in the receptacle preparatory to subsequent use.

Another feature of the invention is that the receiving member may be reattached to the upper end of the receptacle after placement of the first and second plates in the receptacle.

Thus, a feature of the present invention is that the device may be readily disassembled and reassembled to facilitate cleaning, sterilization, and placement of a new indicating strip in the device for subsequent use.

Yet another feature of the invention is that the device assures assembly by the user in a correct manner.

Further features will become more fully apparent in the following description of the embodiments of this invention and from the appended claims.

DESCRIPTION OF THE DRAWINGS

In the drawings:

FIG. 1 is a fragmentary side elevational view of a urine measuring device of the present invention;

FIG. 2 is a fragmentary end elevational view of the device of FIG. 1;

FIG. 3 is a fragmentary side exploded view of the device of FIG. 1;

FIG. 4 is a top plan view of a receiving member for the device of FIG. 1;

FIG. 5 is a top plan view of a receptacle for the device of FIG. 1;

FIG. 6 is a bottom plan view of the receiving member of FIG. 4;

FIG. 7 is a fragmentary sectional view of the receiving member and receptacle of the device of FIG. 1;

FIG. 8 is a fragmentary sectional view taken substantially as indicated along the line 8—8 of FIG. 7;

FIG. 9 is a fragmentary sectional view taken substantially as indicated along the line 9—9 of FIG. 7;

FIG. 10 is a fragmentary sectional view taken substantially as indicated along the line 10—10 of FIG. 7;

FIG. 11 is a front plan view of a first plate for the device of FIG. 1;

FIG. 12 is a rear plan view of the first plate of FIG. 11;

FIG. 13 is a sectional view taken substantially as indicated along the line 13—13 of FIG. 11;

FIG. 14 is a front plan view of a second plate for the device of FIG. 1;

FIG. 15 is a rear plan view of the second plate of FIG. 14;

FIG. 16 is a sectional view taken substantially as indicated along the line 16—16 of FIG. 3 with the first and second plates correctly positioned in the receptacle;

FIG. 17 is a fragmentary elevational view, taken partly in section, of the device with the first and second plates correctly positioned in the receptacle;

FIG. 18 is a fragmentary elevational view, taken partly in section, of the receptacle with the first and second plates incorrectly positioned in the receptacle;

FIG. 19 is a sectional view taken substantially as indicated along the line 19—19 of FIG. 18;

FIG. 20 is a lower plan view of the receptacle;

FIG. 21 is a fragmentary perspective view illustrating a tubular extension defining an outlet port at a lower end of the receptacle;

FIG. 22 is a fragmentary front plan view of a container for the device of FIG. 1;

FIG. 23 is a fragmentary sectional view taken substantially as indicated along the line 23—23 of FIG. 22; and FIG. 24 is a fragmentary sectional view taken substantially as indicated along the line 24—24 of FIG. 22.

DESCRIPTION OF THE PREFERRED EMBODIMENTS

Referring now to FIGS. 1-3, there is shown a device generally designated 30 for measuring and collecting a discharge of liquid, such as urine. The device 30 includes a hollow transparent receptacle generally designated 32 having a chamber 34, a container 36 releasably attached to a lower end of the receptacle 32, and a receiving member 38 releasably attached to an upper end of the receptacle 32.

With reference to FIGS. 3, and 11-13, the receptacle 32 has an elongated first plate 40 having an elongated narrow slot 42, and a pair of opposed side edges 44a and 44b which taper from an upper end 46 of the first plate toward a lower end 48 of the first plate 40. The first plate 40 also has a plurality of transverse spaced bars 50 which extend across the slot 42 and connect opposed sides of the first plate in order to reinforce the first plate longitudinally along the slot 42, with the bars 50 being located on a front face 52 of the first plate 40. As shown, the first plate 40 also has a lower boss 54 extending outwardly from a rear face 56 of the first plate 40 adjacent the juncture of the side edge 44b and a lower edge 55 of the first plate 40.

Referring to FIGS. 14 and 15, the receptacle 32 has an elongated second plate 58 having a front face 60, a rear face 62, and a pair of tapered side edges 64a and 64b extending from an upper end 66 to a lower end 68 of the second plate 58. The second plate 58 also has an abutment member 70 extending laterally across the second plate 58 on the rear face 62 adjacent the lower end 68 of the second plate 58. As shown, an elongated indicating plate 72 extends outwardly from a central portion of the second plate front face 60, with the indicating plate 72 having an upper end 74 spaced slightly below the upper end 66 of the second plate 58, and a lower end 76 extending below the lower end 68 of the second plate 58. The indicating plate 72 has a pair of spaced upper and lower pins 78a and 78b, with the upper pin 78a extending outwardly from one surface 80 of the indicating plate 72 adjacent the upper end 74 of the indicating plate 72, and with the lower pin 78b extending outwardly from the one surface 80 adjacent the lower end 76 of the indicating plate 72.

With reference to FIG. 3, the device has an elongated indicating strip 82 having apertures 84a and 84b adjacent upper and lower ends 86a and 86b, respectively, of the indicating strip 82, with the distance between the apertures 84a and b being approximately equal to the distance between the pins 78a and b of the indicating plate 72, and with the diameter of the apertures 84a and b being approximately equal to the diameter of the pins 78a and b. Thus, the indicating strip 82 may be releasably attached to the indicating plate 72 with the pins 78a and b received through the strip apertures 84a and b, respectively, such that an indicating strip may be placed upon or removed from the indicating plate 72, as desired by the user. The indicating strip 82 is sensitive to contact or wetting by liquid, such as urine, and, as will be seen below, the indicating strip 82 is retained in an upright position in the receptacle 32 by the indicating plate 72 and second plate 58, such that the indicating strip provides an indication of the maximum height of liquid reached in the receptacle during the urine discharge. Any suitable material may be utilized for the indicating strip 82, such as a material which changes color upon contact by the liquid. For example, a methylene blue compound or rhodamine may be utilized on the strip 82 to obtain the desired indication. Flow rate information may be determined by suitable indicia I spaced along the strip.

With reference to FIGS. 1-3, 5, 16, and 17, the receptacle 32 has a lower wall 88 at a lower end 90 of the receptacle 32, and an outer wall 92 comprising an opposed pair of generally flat upright sidewalls 94a and 94b which taper slightly from an upper end 96 of the receptacle 32 to the lower end 90, and comprising a pair of arcuate upright end walls 98a and 98b connecting the sidewalls 94a and b. As shown, the sidewalls 94a and b have a pair of opposed first grooves 100a and 100b extending substantially the height of the sidewalls 94a and b, and a pair of inner first bosses 102a and 102b extending upwardly from the lower wall 88 at a location slightly forward of the grooves 100a and b on the sidewalls 94a and b. The sidewalls 94a and b also have a pair of opposed second grooves 104a and 104b intermediate the first grooves 100a and b and the end wall 98b and extending from the receptacle upper end 96 to a location spaced slightly above the lower wall 88. Also, the receptacle 32 has a pair of second bosses 106a and 106b extending upwardly from the lower wall 88 on the sidewalls 94a and b at a location slightly forward of the second grooves 104a and b.

With the receiving member 38 removed from the receptacle 32, the first plate 40 may be positioned in the receptacle 32 through an upper opening 107 of the receptacle with the first plate side edges 44a and 44b being received in the receptacle first grooves 100a and b, respectively, and with the lower end 48 of the first plate 40 being received in a transverse groove 108 in the lower receptacle wall 88. Also, the second plate 58 may be inserted through the opening 107 into the receptacle 32 with the side edges 64a and b being received in the second grooves 104a and b, respectively, until the lower end 76 of the indicating plate 72 is located adjacent the lower receptacle wall 88. The tapered sidewalls 94a and b and tapered plates 40 and 58 facilitate insertion of the plates 40 and 58 into the receptacle 32, and also enhance sealing between the plates 40 and 58 and the receptacle after insertion of the plates.

In the inserted configuration, the first plate 40 defines a channel 110 intermediate the first plate 40 and receptacle front end wall 98a, the second plate 58 defines a passageway 112 intermediate the second plate 58 and the receptacle rear end wall 98b, and the first plate 40 and second plate 58 define a compartment 114 intermediate the first and second plates 40 and 58. As shown, the upper ends 46 and 66 of the first and second plates 40 and 58, respectively, are located at the upper end 96 of the receptacle 32 in order that the receiving member 38 may be placed upon the receptacle 32, with the lower end 68 of the second plate 58 defining a space 116 intermediate the second plate 58 and the lower wall 88, such that the space 116 communicates between the passageway 112 and the compartment 114. In this configuration, the front face 52 of the first plate 40 faces toward the end wall 98a, with the boss 54 being directed toward the second plate 58, and the slot 42 communicates between the compartment 114 and channel 110. Also, the front face 60 of the second plate 58 faces toward the first plate 40 with the indicating plate 72 located in the compartment 114, such that the indicating strip 82 is retained in the compartment 114. Thus, in the above-described correct orientation of the first and second plates 40 and 58, the plates may be completely inserted into the receptacle 32 preparatory to placement of the receiving member 38 on the receptacle 32.

However, with reference to FIGS. 18 and 19, in the event that the first plate 40 is incorrectly positioned in the receptacle 32 with the front face 52 facing away from the receptacle end wall 98a, the boss 54 of the first plate 40 strikes the receptacle first boss 102a which obstructs complete insertion of the first plate 40 into the receptacle 32, such that the upper end 46 of the first plate 40 protrudes above the upper end 96 of the receptacle 32. Similarly, in the event that the second plate 58 is incorrectly inserted into the receptacle 32 with the indicating plate 72 positioned in the passageway 112, the abutment member 70 strikes against the second bosses 106a and b, thus preventing complete insertion of the second plate 58 into the receptacle 32, such that the upper end 66 of the second plate 58 protrudes above the upper end 96 of the receptacle 32. Also, the length of the first plate 40 is substantially greater than the length of the second grooves 104a and b, such that the upper end 46 of the first plate 40 protrudes above the upper end 96 of the receptacle 32 if the first plate 40 is incorrectly positioned in the second grooves 104a and b, thus preventing reversal of the first and second plates 40 and 58 relative to the first and second grooves. Hence, in the event of incorrect positioning of either the first or second plates 40 or 58 in the receptacle, the respective protruding upper end or ends prevents placement of the receiving member 38 on the receptacle 32. Thus, the user is required to correctly position the first and second plates 40 and 58 in the receptacle 32 prior to placement of the receiving member 38 on the receptacle 32, and, in this manner, the device 30 assures correct placement of the plates in the receptacle 32.

With reference to FIGS. 1-4, and 6-10, the receiving member 38 has an upright back wall 118, a lower wall 120, and a pair of sidewalls 122a and 122b connecting the back and lower walls 118 and 120, such that the walls define a cavity 124 and an inlet port 126 communicating with the cavity 124 for passage of the discharge into the cavity 124. When the receiving member 38 is positioned on the receptacle 32, the lower wall 120 covers the channel 110 and compartment 114, and the lower wall 120 and back wall 118 define a lower outlet opening 128 communicating between the cavity 124 and the receptacle passageway 112. As shown, the upper end edge 130 of the sidewalls 122a and b and the back wall 118, which define the port 126, is curved outwardly to prevent a sharp edge being presented toward the patient during voiding, particularly a female patient.

The receiving member 38 has a depending skirt 132 defining a pair of opposed generally planar lower side edges 134a and 134b of the receiving member 38, and a pair of opposed arcuate end edges 136a and 136b connecting the side edges 134a and b. The receiving member 38 has a depending directing plate 138 defining a forward portion of the outlet opening 128 and extending below the skirt 132, such that the plate 138 extends below the upper end 66 of the second plate 58 in the passageway 112 when the receiving member 38 is attached to the receptacle 32. The receiving member 38 also has an arcuate flange 140 depending from the lower wall 120 and defining a rearward portion of the outlet opening 128, with the flange 140 being spaced from the skirt 132 and extending rearwardly from the plate 138, such that the flange 140 and skirt 132 define an arcuate groove 142 intermediate the flange 140 and the skirt edge 136b. Further, the skirt 132 has a rim 144 defining a lower surface in the plane of the inner surface 145 of the arcuate groove 142, such that the upper end 96 of the receptacle 32 seats upon the inner surface 145 of the groove 142 and the rim 144 when the receiving member 38 is attached to the receptacle 32.

The skirt side edges 134a and b of the receiving member 38 have a pair of elongated inner flanges 146a and 146b defining associated grooves 148a and 148b between the respective flanges 146a and b and the rim 144. Also, the skirt end edge 136a has a notch 150 at the lower end of the skirt. As shown, the receptacle 32 has an outwardly directed rim 152 at the upper end 96 of the receptacle 32, and a boss 154 extending outwardly from the receptacle wall 98a at the upper end 96 of the receptacle 32.

When the receiving member 38 is correctly positioned on the receptacle 32, the skirt 132 of the receiving member 38 receives the upper end 96 of the receptacle 32 within the side edges 134a and b and end edges 136a and b, with the receptacle boss 154 being received in the receiving member notch 150 to assure that the receiving member has been correctly positioned on the receptacle 32. In this configuration, a skirt side edge 134a covers the upper end of the receptacle sidewall 94a, the skirt side edge 134b covers the upper end of the receptacle sidewall 94b, the skirt end edge 136a covers the upper end of the receptacle end wall 98a, and the skirt end edge 136b covers the upper end of the receptacle end wall 98b, with the upper receptacle end wall 98b being received in the arcuate groove 142, and with the upper end 96 of the receptacle 32 abutting against the rim 144 and the inner surface 145 of the arcuate groove 142. Also, the receptacle rim 152 in the region of the receptacle sidewalls 94a and b snaps over the skirt flanges 146a and b into the grooves 148a and b in order to releasably lock the receiving member 38 onto the upper end of the receptacle 32. Thus, the receiving member 38 may be readily attached to the receptacle 32 through use of the cooperating skirt flanges 146a and b and the receptacle rim 152, and the receiving member 38 may be removed from the receptacle 32 by pulling on the receiving member in order to release the receptacle rim 152 from the grooves 148a and b for passage over the skirt flanges 146a and b. In the event that the user attempts to incorrectly position the receiving member 38 on the receptacle 32 with the receptacle end wall 98a in the receiving member groove 142, the receptacle boss 154 strikes against the skirt edge 136b and prevents placement of the receiving member onto the receptacle. Thus, in this manner, the device assures that the receiving member 38 will be correctly positioned on the receptacle 32 during use.

The receiving member skirt 132 has a pair of opposed inwardly directed flanges 156a and 156b located above the associated side edges 134a and b, respectively, such that the flanges 156a and b of the attached receiving member abut against opposed ends of the first plate 40 at the upper end 46 of the first plate 40 in order to retain the first plate 40 at the desired position in the receptacle with the lower end 48 of the first plate 40 received in the lower receptacle groove 108. Also, when the receiving member 38 is correctly positioned upon the receptacle 32, the lower wall 120 of the receiving member 38 bears against the upper end 66 of the second plate 58 in order to retain the second plate 58 at the desired position in the receptacle.

As shown in FIGS. 1 and 2, a strip 157 of liquid porous material is removably received in the receiving member cavity 124 intermediate the inlet port 126 and the outlet opening 128, such that at least a portion of the strip 157 covers the outlet opening. The strip 157 may be made of any suitable material, such as open cell polyurethane. The strip 157 is preferably treated with a coating of a foam preventing material, such as by dipping the strip into a solution of an anti-foam agent. A suitable solution for treating the strip is a silicone defoamer Antifoam A Compound, a mixture of silica gel and dimethicone that has an average chain length of 200 to 350 dimethylsiloxane units, sold by Dow Corning Corporation, and diluted by 25 parts of carbon-tetrachloride to 1 part of the antifoam compound. In use, the strip 157 breaks up the urine discharge passing into the cavity 124, and provides an even flow of the discharge through the opening 128 into the passageway 112 to permit a more accurate determination of data associated with the discharge in the compartment 114. The strip 157 also prevents splashing of the discharge against the patient using the device. Additionally, the treated strip 157 prevents foaming of the urine discharge in the cavity 124, and thus prevents collection of foam in the cavity 124.

With reference to FIGS. 1-3, 16, 17, 20, and 21, the receptacle 32 has a lower tubular extension 160 depending below the lower wall 88 and defining an outlet port 162 communicating with the channel 110 for passage of liquid out of the receptacle 32. As shown, the extension 160 has a pair of inner opposed generally triangular-shaped protuberances 164 and 166 at a lower end 168 of the extension 160.

With reference to FIGS. 1-3, and 22-24, the container 36 has a pair of opposed transparent flexible sidewalls 170a and 170b which are sealed together around their edges to define a chamber 172 intermediate the sidewalls 170a and b. The container 36 also has a support member 174 having a generally planar lower wall 176 having its edges secured to the front sidewall 170a peripherally around an opening 178 in the sidewall 170a.

The support member 174 has a first annular section 180 extending upwardly from the lower wall 176 and defining a passageway 182 communicating with the container chamber 172. The first section 180 has an outside diameter slightly less than the inside diameter of the receptacle extension 160, such that the first section 180 may be received in the extension 160 with the passageway 182 communicating between the receptacle channel 110 and container chamber 172. As shown, the first section 180 has a pair of opposed outwardly directed flanges 184a and 184b at an outer end 186 of the first section 180. The support member 174 also has a second outer annular section 188 extending upwardly from the lower wall 176, with the second section 188 having a greater height than that of the first section 180, and being spaced from the first section 180, such that the first and second sections 180 and 188 define an annular groove 189 intermediate the first and second sections 180 and 188 to receive the lower end of the receptacle extension 160. As shown, the lower wall 176 has a pair of spaced slots 190a and 190b communicating between an inner end of the groove 189 and the container chamber 172 to permit drainage of liquid from the groove 189 into the chamber 172. The first section 180 has a pair of crossed reinforcement members 192a and 192b to enhance the rigidity of the first section 180 as it is secured onto the receptacle extension 160. Also, the inner ends of the reinforcement members 192a and b extend past the lower wall 176 of the support member 174 to engage against the container sidewall 170b in the region of the passageway 182 to assure that the back sidewall 170b remains spaced from the support member 174 in the region of the passageway 182 and prevent obstruction of the passageway 182 during passage of liquid through the passageway into the container chamber 172.

The container 36 may be releasably attached to the receptacle 32 by placement of the receptacle extension 160 in the support member groove 189 with the flanges 184a and b located intermediate the extension protuberances 164 and 166. Next, the container 36 is twisted relative to the receptacle 32 in order to rotate the first section 180 in the receptacle extension 160, such that the flanges 184a and b engage against upper surfaces of the respective protuberances 164 and 166 in the extension, with the flanges and protuberances cooperating to releasably secure the first section 180 onto the receptacle extension 160. The container 36 may be removed from the receptacle 32 by rotating the first section 180 in an opposite angular direction within the tubular section 160 to place the flanges 184a and b intermediate the protuberances 164 and 166, after which the first section 180 may be withdrawn from the receptacle extension 160. When the container 36 is secured to the receptacle 32, the tubular extension 160 is received in the annular groove 189 intermediate the first and second sections 180 and 188 with the passageway 182 communicating between the receptacle channel 110 and the container chamber 172.

The container 36 also has a cap 194 attached to the support member 174 by a strap 196. The cap 194 may be releasably attached to the second section 188 to close the outer end of the passageway 182. As shown, the support member 174 has an aspirating port 198 extending through the support member 174 to the container chamber 172. The container 36 also has a second cap 200 attached to the support member 174 by a strap 202, with the cap 200 being releasably received in the port 198 to close the port 198.

When it is desired to use the device, an indicating strip is attached to the pins 78a and b of the indicating plate 72, and the first and second plates 40 and 58 are positioned in the receptacle 32. The receiving member 38 may then be attached to the upper end of the receptacle 32, and the container 36 may be attached to the tubular extension 160 of the receptacle 32. The inlet port 126 of the device 30 is then positioned by a patient in privacy to receive the discharge. As the liquid discharge passes into the receiving member 38 of the device 30, the discharge is directed by the receiving member 38 through the outlet opening 128 into the passageway 112, and through the space 116 to the compartment 114, for collection in the receptacle 32. As the discharge continues, the liquid collects in the lower part of the compartment 114 and passes from the compartment 114 through the slot 42 into the channel 110. From the channel 110, the liquid passes through the outlet port 162 into the lower container 36 for collection in the chamber 172. As the rate of discharge into the receptacle increases, the height of liquid in the compartment 114 also increases while the liquid drains through the slot 42 into the channel 110.

For a given rate of flow of the discharge into the receptacle the liquid attains a fixed height in the compartment 114, and the liquid passes at a fixed rate of flow through the slot 42. Hence, if the rate of flow of the liquid discharge into the receptacle increases, the height of liquid in the compartment 114 rises an additional amount, and the rate of flow through the slot 42 also increases, since the liquid flows through a larger vertical portion of the slot 42. Thus, as long as the rate of flow of the discharge into the receptacle increases, the height of liquid in the compartment 114 continues to rise, and the rate of flow of liquid through the slot 42 also increases. When the flow rate of the incoming discharge abates, the liquid drains from the compartment 114 into the channel 110 faster than it enters the compartment 114 and the height of the liquid in the compartment 114 begins to subside.

Peak flow rate of the incoming liquid discharge may be defined as the maximum rate of flow of the discharge. Since the height of liquid in the compartment 114 rises or lowers responsive to an increase or decrease, respectively, of the flow rate of the incoming discharge, it is apparent that the maximum height of liquid attained in the compartment 114 during the discharge serves as an indication of the approximate peak flow rate of the discharge. Although anomalies in the discharge, such as a momentary surge of the discharge, may not be ultimately reflected in the maximum liquid height in the compartment, due, in part, to the lag between the time the discharge enters the receptacle and the time it enters the compartment, the device determines the peak flow rate with sufficient accuracy for such purposes as are under discussion. In particular, a urine stream during voiding has a relatively slow rate of change of flow rate, and the device of the present invention indicates a peak flow rate for the discharge which is sufficiently accurate for purposes of diagnosing the patient.

It is possible that the approximate peak flow rate of the urine discharge may be determined by observing the highest level of liquid accumulated in the compartment 114 during the discharge. Direct reading by the patient may be impractical or difficult during self-administration of the apparatus as thus far described if the apparatus is utilized to collect a discharge of liquid during voiding, and it is desirable that the device be self-administered in order to alleviate any psychological problem of the patient which might be caused by observation of the receptacle during voiding.

Accordingly, the indicating strip 82 has been provided to automatically record the approximate maximum height of liquid collected in the compartment 114 during the liquid discharge. After the liquid discharge has been completed, a direct reading of the approximate peak flow rate may be determined by the indicia I on the indicating strip 82. Alternatively, the indicia I may be placed on the wall of the transparent receptacle 32.

The receptacle may be calibrated against known constant flow rates of a discharge passing into the receptacle to determine the appropriate location for the indicia I on the indicating strip 82. That this may be readily accomplished is apparent from the fact that the peak flow rate for a discharge having a constant flow rate is the value of the constant flow rate itself. Accordingly, when the discharge of constant flow rate is directed into the receptacle, liquid rises in the compartment to a level at which liquid entering the compartment is offset by liquid draining from the compartment 114 into the channel 110, and the receptacle 32 or strip 82 is marked at this height for peak flow rate by the value of the flow rate of the constant discharge.

As noted above, once the rate of flow of the liquid discharge into the receptacle abates, the height of liquid in the compartment 114 subsides, and the approximate peak flow rate has already been determined on the indicating strip 82. During the remainder of the liquid discharge, the liquid continues to drain from the compartment 114 into the channel 110 until the discharge is terminated and drainage from the compartment 114 to the channel 110 eventually stops. Since the liquid drains from the channel 110 of the receptacle 32 into the lower container 36, the volume of liquid which collects in the lower container 36 during the liquid discharge may be readily determined by suitable indicia I' on the transparent sidewalls of the container.

Since the patient may use the device without observation, unnatural voiding or failure to void which may occur when a patient voids under observation is prevented. After voiding, the patient merely summons the physician or nurse, who then uses the device to diagnose the patient's voiding. As previously indicated, the indicating strip 82 may be used to obtain a reading of the peak flow rate of the urine discharge by the indicia I on the strip 82. The lower container may be removed from the receptacle 32, and the cap 200 may be removed from the port 198 to permit aspiration of a urine sample with a pipette through the port 198, after which the container may be closed by caps 194 and 200 and discarded, if desired. The receiving member 38 may be removed from the receptacle 32, and the first and second plates 40 and 58 may be removed from the receptacle 32 to facilitate cleaning and sterilization of the device, if desired. Also, a new indicating strip may be placed on the second plate 58, and the first and second plates 40 and 58 may be placed in the receptacle 32, after which the receiving member 38 may be attached to the receptacle 32 to permit subsequent use of the device. Thus, in accordance with the present invention, the device 30 may be cleaned and sterilized in a simplified manner for future use to reduce the cost of diagnosing various patients, with the device assuring that the various parts are assembled in a correct manner. As illustrated in FIGS. 1 and 4, the receiving member 38 may have a hook 158 connected to the back wall 118 by a flexible strap 159 adjacent an upper end of the receiving member 38. The hook 158 may be utilized by the patient to temporarily place the device 30 on a fixture, such as the back of a chair (not shown), before or after voiding, or both.

The foregoing detailed description is given for clearness of understanding only, and no unnecessary limitations should be understood therefrom, as modifications will be obvious to those skilled in the art.

We claim:

1. A device for measuring a discharge of urine, comprising:
   a hollow open topped receptacle having upright walls and a lower wall defining a chamber, an elongated first upright plate extending laterally across the inside of the receptacle substantially the height of the chamber from said lower wall to a location adjacent an upper end of the receptacle, said first plate defining channel means intermediate the first plate and an upright wall of the receptacle, said first plate having slot means extending longitudinally along the first plate, and said receptacle having an elongated second upright plate extending laterally across the inside of the receptacle from a location adjacent an upper end of the receptacle to a location adjacent a lower end of the receptacle, with said second plate defining a compartment intermediate the first and second plates, passageway means intermediate the second plate and an upright wall of the receptacle, and a space adjacent said lower wall communicating between said passageway means and said compartment;
   a fluid receiving member having a lower wall and sidewalls defining a cavity, an inlet port communicating with the cavity for passage of the discharge into the cavity, and a lower outlet opening communicating with the cavity for passage of the discharge out of the cavity said lower wall defining fluid flow means for directing fluid to said receiving member outlet opening;
   means for releasably attaching a lower portion of the receiving member to said open top of the receptacle with said receiving member lower wall covering the channel means and compartment, and with the receiving member outlet opening communicating with the passageway means when said receiver and receptacle are in assembly; and
   means for indicating the maximum height of liquid collected in said compartment.

2. The device of claim 1 wherein said receiving member includes a directing plate depending from a rearward portion of the receiving member lower wall and defining a front portion of the outlet opening, said directing plate extending into the passageway means below an upper end of said second plate when the receiving member is attached to the receptacle.

3. The device of claim 1 wherein the slot means of the first plate comprises an elongated narrow slot, and in which the first plate includes a plurality of transverse spaced bars extending across said slot and connecting sides of the first plate on opposed sides of the slot.

4. The device of claim 1 including means for releasably receiving said first plate through the open top of the receptacle when the receiving member is removed from the receptacle.

5. The device of claim 4 wherein the plate receiving means comprises a pair of opposed longitudinal grooves in opposed sidewalls of the receptacle to receive opposed sides of the first plate.

6. The device of claim 5 wherein said opposed sidewalls are generally flat and tapered from upper to lower end portions of the receptacle, and in which the first plate is tapered from an upper to lower portion of the first plate.

7. A device for measuring a discharge of urine, comprising:
   a hollow receptacle having upright walls and a lower wall defining a chamber, an elongated removable first upright plate extending laterally across the inside of the receptacle substantially the height of the chamber from said lower wall to a location adjacent an upper end of the receptacle, said first plate defining channel means intermediate the first plate and an upright wall of the receptacle, said first plate having slot means extending longitudinally along the first plate, and said receptacle having an elongated second upright plate extending laterally across the inside of the receptacle from a location adjacent an upper end of the receptacle to a location adjacent a lower end of the receptacle, with said second plate defining a compartment intermediate the first and second plates, passageway means intermediate the second plate and an upright wall of the receptacle, and a space adjacent said lower wall communicating between said passageway means and said compartment;
   a fluid receiving member having walls defining a cavity and an inlet port communicating with the cavity for passage of the discharge into the cavity, said walls defining a lower outlet opening communicating between the cavity and passageway means for passage of the discharge from the receiving member into the receptacle;
   means for removably positioning the first plate in the receptacle in a predetermined orientation; and
   means for indicating the maximum height of liquid collected in said compartment.

8. A device for measuring a discharge of urine, comprising:
   a hollow receptacle having upright walls and a lower wall defining a chamber, an elongated first upright plate extending laterally across the inside of the receptacle substantially the height of the chamber from said lower wall to a location adjacent an upper end of the receptacle, said first plate defining channel means intermediate the first plate and an upright wall of the receptacle, said first plate having slot means extending longitudinally along the first plate, and said receptacle having an elongated removable second upright plate extending laterally across the inside of the receptacle from a location adjacent an upper end of the receptacle to a location adjacent a lower end of the receptacle, with said second plate defining a compartment intermediate the first and second plate, passageway means intermediate the second plate and an upright wall of the receptacle, and a space adjacent said lower wall communicating between said passageway means and said compartment;
   a fluid receiving member having walls defining a cavity and an inlet port communicating with the cavity for passage of the discharge into the cavity, said walls defining a lower outlet opening communicating between the cavity and passageway means for passage of the discharge from the receiving member into the receptacle;
   means for removably positioning the second plate in the receptacle in a predetermined orientation; and
   means for indicating the maximum height of liquid collected in the compartment.

9. A device for measuring a discharge of urine, comprising:

a receiving member having an inlet port to receive the discharge;

a receptacle having a chamber to receive the discharge from the receiving member, means for measuring a dynamic characteristic of the discharge including means for indicating the maximum height of liquid collected in the receptacle, and a lower tubular extension defining an outlet port for passage of the discharge from the receptacle, with said extension having a pair of inner opposed generally triangular-shaped protuberances at a lower end of said extension; and a container having a chamber defined by a pair of opposed, flexible sidewalls, and a support member secured to one of said flexible sidewalls of the container, said support member including a first annular section defining a passageway communicating with the container chamber, said first section having an outside diameter slightly less than the inside diameter of said extension and being receivable in the extension with the passageway communicating between the chambers of the receptacle and container, said first section having a pair of opposed outwardly directed flanges adjacent an outer end of the first section to engage upper surfaces of the respective protuberances in said extension, such that said flanges and protuberances cooperate to releasably secure said first section to said extension responsive to rotation of the first section in the extension relative to said receptacle, said passageway including a pair of reinforcement members extending across the passageway of said first section, said reinforcement members including inner ends extending past said one container sidewall to space the other container sidewall from said one sidewall.

10. The device of claim 9 wherein said support member includes a second outer annular section defining an annular groove intermediate the first and second sections to receive the lower end of said extension when the container is attached to the receptacle.

11. The device of claim 10 including slot means extending through the support member adjacent a lower portion of said groove to permit drainage from the groove into the container chamber.

12. A device for measuring a discharge of urine, comprising:

a hollow receptacle having upright walls and a lower wall defining a chamber, an elongated removable first upright plate extending laterally at a first location across the inside of the receptacle substantially the height of the chamber from said lower wall to a location adjacent an upper end of the receptacle, said first plate defining channel means intermediate the first plate and an upright wall of the receptacle, said first plate having slot means extending longitudinally along the first plate, and said receptacle having a elongated removable second upright plate extending laterally at a second location across the inside of the receptacle from a location adjacent an upper end of the receptacle to a location adjacent a lower end of the receptacle, with said second plate defining a compartment intermediate the first and second plates, passageway means intermediate the second plate and an upright wall of the receptacle, and a space adjacent said lower wall communicating between said passageway means and said compartment;

a fluid receiving member having walls defining a cavity and an inlet port communicating with the cavity for passage of the discharge into the cavity, said walls defining a lower outlet opening communicating between the cavity and passageway means for passage of the discharge from the receiving member into the receptacle;

means for removably positioning the first plate at the first location in the receptacle in a predetermined orientation;

means for removably positioning the second plate at the second location in the receptacle in a predetermined orientation; and means for indicating the maximum height of liquid collected in the compartment.

13. A device for measuring a discharge of urine, comprising:

a hollow receptacle having upright walls and a lower wall defining a chamber, an elongated first upright plate extending laterally across the inside of the receptacle substantially the height of the chamber from said lower wall to a location adjacent an upper end of the receptacle, said first plate defining channel means intermediate the first plate and an upright wall of the receptacle, said first plate having slot means extending longitudinally along the first plate, and said receptacle having an elongated second upright plate extending laterally across the inside of the receptacle from a location adjacent an upper end of the receptacle to a location adjacent a lower end of the receptacle, with said second plate defining a compartment intermediate the first and second plates, passageway means intermediate the second plate and an uright wall of the receptacle, and a space adjacent said lower wall communicating between said passageway means and said compartment;

a fluid receiving member having a lower wall and sidewalls defining a cavity, an inlet port communicating with the cavity for passage of the discharge into the cavity, and a lower outlet opening communicating with the cavity for passage of the discharge out of the cavity;

means for releasably attaching a lower portion of the receiving member to an upper portion of the receptacle with said receiving member lower wall covering the channel means and compartment, and with the receiving member outlet opening communicating with the passageway means;

means for indicating the maximum height of liquid in the compartment; and means for releasably receiving said first plate through an upper opening of the receptacle when the receiving member is removed from the receptacle, said plate receiving means comprising a pair of opposed longitudinal grooves in opposed sidewalls of the receptacle to receive opposed sides of the first plate, said receptacle including an inner first boss adjacent at least one of said grooves above said lower wall, and in which said first plate includes a cooperating second boss adjacent a lower end of the first plate, said first and second bosses being arranged to strike and obstruct complete insertion of the first plate into the receptacle in a first undesired orientation of the first plate relative to the receptacle, and permit complete insertion of the first plate in a second opposed desired orientation of the first plate relative to the receptacle.

14. A device for measuring a discharge of urine, comprising:
a hollow receptacle having upright walls and a lower wall defining a chamber, an elongated first upright plate extending laterally across the inside of the receptacle substantially the height of the chamber from said lower wall to a location adjacent an upper end of the receptacle, said first plate defining channel means intermediate the first plate and an upright wall of the receptacle, said first plate having slot means extending longitudinally along the first plate, and said receptacle having an elongated second upright plate extending laterally across the inside of the receptacle from a location adjacent an upper end of the receptacle to a location adjacent a lower end of the receptacle, with said second plate defining a compartment intermediate the first and second plates, passageway means intermediate the second plate and an upright wall of the receptacle, and a space adjacent said lower wall communicating between said passageway means and said compartment;
a fluid receiving member having a lower wall and sidewalls defining a cavity, an inlet port communicating with the cavity for passage of the discharge into the cavity, and a lower outlet opening communicating with the cavity for passage of the discharge out of the cavity;
means for releasably attaching a lower portion of the receiving member to an upper portion of the receptacle with said receiving member lower wall covering the channel means and compartment, and with the receiving member outlet opening communicating with the passageway means;
means for indicating the maximum height of liquid collected in the compartment;
means for releasably receiving said first plate through an upper opening of the receptacle when the receiving member is removed from the receptacle; and
means for permitting complete insertion of the first plate into the receptacle in a first desired orientation of the first plate relative to the receptacle, and for preventing complete insertion of the first plate into the receptacle in a second opposed undesirable orientation of the first plate relative to the receptacle.

15. A device for measuring a discharge of urine, comprising:
a hollow receptacle having upright walls and a lower wall defining a chamber, an elongated first upright plate extending laterally across the inside of the receptacle substantially the height of the chamber from said lower wall to a location adjacent an upper end of the receptacle, said first plate defining channel means intermediate the first plate and an upright wall of the receptacle, said first plate having slot means extending longitudinally along the first plate, and said receptacle having an elongated second upright plate extending laterally across the inside of the receptacle from a location adjacent an upper end of the receptacle to a location adjacent a lower end of the receptacle, with said second plate defining a compartment intermediate the first and second plates, passageway means intermediate the second plate and an upright wall of the receptacle, and a space adjacent said lower wall communicating between said passageway means and said compartment, said second plate including an outwardly directed indicating plate extending substantially the height of the chamber in said compartment;
an elongated indicating strip;
means for releasably securing said indicating strip to the indicating plate;
a fluid receiving member having a lower wall and sidewalls defining a cavity, an inlet port communicating with the cavity for passage of the discharge into the cavity, and a lower outlet opening communicating with the cavity for passage of the discharge out of the cavity; and
means for releasably attaching a lower portion of the receiving member to an upper portion of the receptacle with said receiving member lower wall covering the channel means and compartment, and with the receiving member outlet opening communicating with the passageway means.

16. The device of claim 15 wherein the securing means comprises a pair of longitudinally spaced pins extending outwardly from the indicating plate and a pair of longitudinally spaced apertures in the indicating strip to receive said pins.

17. The device of claim 16 wherein a lower end of the second plate is spaced from the lower receptacle wall, in which a lower end of the indicating plate is located adjacent the lower receptacle wall, and in which said pins are located adjacent upper and lower ends of the indicating plate.

18. The device of claim 15 including means for releasably receiving said second plate through an upper opening of the receptacle when the receiving member is removed from the receptacle.

19. The device of claim 18 including means for permitting complete insertion of the second plate into the receptacle in a first orientation with the indicating plate located in the compartment, and for preventing complete insertion of the second plate into the receptacle in a second opposed orientation with the indicating plate located in the passageway means.

20. The device of claim 18 wherein the receiving means comprises a pair of opposed longitudinal grooves in opposed sidewalls of the receptacle to receive opposed sides of the second plate.

21. The device of claim 20 wherein said receptacle includes boss means adjacent at least one of said grooves above said lower wall, and in which said second plate includes cooperating abutment means adjacent a lower end of the second plate, said boss means and abutment means being arranged to strike and obstruct insertion of the second plate into the receptacle in a first orientation with the indicating plate located in the passageway means, and permit complete insertion of the second plate in a second opposed orientation with the indicating plate located in said compartment.

22. The device of claim 20 wherein said opposed sidewalls are generally flat and tapered from upper to lower end portions of the receptacle, and in which the second plate is tapered from an upper to lower portion of the second plate.

23. A device for measuring a discharge of urine, comprising:
a hollow receptacle having upright walls and a lower wall defining a chamber, an elongated first upright plate extending laterally across the inside of the receptacle substantially the height of the chamber from said lower wall to a location adjacent an upper end of the receptacle, said first plate defining channel means intermediate the first plate and an upright wall of the receptacle, said first plate having slot means extending longitudinally along the first plate, and said receptacle having an elongated second upright plate extending laterally across the inside of the receptacle from a location adjacent an upper end of the receptacle to a location adjacent a lower end of the receptacle, with said second plate defining a compartment intermediate the first and second plates, passageway means intermediate the second plate and an upright wall of the receptacle, and a space adjacent said lower wall communicating between said passageway means and said compartment;

a fluid receiving member having walls defining a cavity and an inlet port communicating with the cavity for passage of the discharge into the cavity, said walls defining a lower outlet opening communicating between the cavity and passageway means for passage of the discharge from the receiving member into the receptacle;

means for removably positioning the first plate in the receptacle;

means for indicating the maximum height of liquid in the compartment; and means for permitting positioning of the first plate in the receptacle with one predetermined face of the first plate facing toward the second plate, and for preventing positioning of the first plate in the receptacle with said one face facing away from the second plate.

24. A device for measuring a discharge of urine, comprising:

a hollow receptacle having upright walls and a lower wall defining a chamber, an elongated first upright plate extending laterally across the inside of the receptacle substantially the height of the chamber from said lower wall to a location adjacent an upper end of the receptacle, said first plate defining channel means intermediate the first plate and an upright wall of the receptacle, said first plate having slot means extending longitudinally along the first plate, and said receptacle having an elongated second upright plate extending laterally across the inside of the receptacle from a location adjacent an upper end of the receptacle to a location adjacent a lower end of the receptacle, with said second plate defining a compartment intermediate the first and second plates, passageway means intermediate the second plate and an upright wall of the receptacle, and a space adjacent said lower wall communicating between said passageway means and said compartment;

a fluid receiving member having walls defining a cavity and an inlet port communicating with the cavity for passage of the discharge into the cavity, said walls defining a lower outlet opening communicating between the cavity and passageway means for passage of the discharge from the receiving member into the receptacle;

means for removably positioning the second plate in the receptacle;

an indicating strip; and means operatively associated with said second plate for supporting the indicating strip on one side of the second plate in the compartment with the strip extending longitudinally along the second plate.

25. The device of claim 24 including means for permitting placement of the second plate in the receptacle with the indicating strip located in the compartment, and for preventing placement of the second plate in the receptacle with the indicating strip located in the passageway means.

26. A device for measuring a discharge of urine, comprising:

a hollow receptacle having upright walls and a lower wall defining a chamber, an elongated first upright plate extending laterally at a first location across the inside of the receptacle substantially the height of the chamber from said lower wall to a location adjacent an upper end of the receptacle, said first plate defining channel means intermediate the first plate and an upright wall of the receptacle, said first plate having slot means extending longitudinally along the first plate, and said receptacle having an elongated second upright plate extending laterally at a second location across the inside of the receptacle from a location adjacent an upper end of the receptacle to a location adjacent a lower end of the receptacle, with said second plate defining a compartment intermediate the first and second plates, passageway means intermediate the second plate and an upright wall of the receptacle, and a space adjacent said lower wall communicating between said passageway means and said compartment;

a fluid receiving member having walls defining a cavity and an inlet port communicating with the cavity for passage of the discharge into the cavity, said walls defining a lower outlet opening communicating between the cavity and passageway means for passage of the discharge from the receiving member into the receptacle;

means for removably positioning the first plate at the first location in the receptacle;

means for removably positioning the second plate at the second location in the receptacle;

means for indicating the maximum height of liquid in the compartment; and means for preventing placement of the first and second plates at said second and first locations, respectively, in the receptacle.

* * * * *